(12) United States Patent
Cho et al.

(10) Patent No.: US 8,046,059 B2
(45) Date of Patent: Oct. 25, 2011

(54) MOBILE DIAGNOSIS DEVICE

(75) Inventors: Ok Kyung Cho, Schwerte (DE); Yoon Ok Kim, Schwerte (DE)

(73) Assignee: Ingo Flore, Dortmund (DE)

( * ) Notice: Subject to any disclaimer, the term of this patent is extended or adjusted under 35 U.S.C. 154(b) by 42 days.

(21) Appl. No.: 11/886,794

(22) PCT Filed: Mar. 16, 2006

(86) PCT No.: PCT/EP2006/002410
§ 371 (c)(1),
(2), (4) Date: Nov. 28, 2007

(87) PCT Pub. No.: WO2006/099988
PCT Pub. Date: Sep. 28, 2006

(65) Prior Publication Data
US 2008/0200823 A1    Aug. 21, 2008

(30) Foreign Application Priority Data
Mar. 21, 2005   (DE) .......................... 10 2005 013 429

(51) Int. Cl.
*A61B 5/0402* (2006.01)

(52) U.S. Cl. .......................... 600/513; 600/509; 600/523

(58) Field of Classification Search .................. 600/483, 600/485, 481, 490, 495, 500, 502, 513, 509, 600/523
See application file for complete search history.

(56) References Cited

U.S. PATENT DOCUMENTS

| | | | |
|---|---|---|---|
| 4,934,382 A | 6/1990 | Barone, Jr. | |
| 4,960,126 A | 10/1990 | Conlon et al. | |
| 5,191,891 A * | 3/1993 | Righter | 600/523 |
| 5,309,916 A | 5/1994 | Hatschek | |
| 6,190,325 B1 * | 2/2001 | Narimatsu | 600/490 |
| 7,215,991 B2 * | 5/2007 | Besson et al. | 600/509 |
| 2001/0012916 A1 | 8/2001 | Deuter | |
| 2002/0087087 A1 | 7/2002 | Oka et al. | |
| 2003/0109901 A1 | 6/2003 | Greatbatch | |
| 2004/0116784 A1 | 6/2004 | Gavish | |
| 2004/0162493 A1 | 8/2004 | Mills | |

FOREIGN PATENT DOCUMENTS

EP        1 317 902        6/2003

OTHER PUBLICATIONS

International Search Report for PCT/EP2006/002410 Jul. 13, 2006.

* cited by examiner

*Primary Examiner* — Carl H Layno
*Assistant Examiner* — Pamela M Bays
(74) *Attorney, Agent, or Firm* — Collard & Roe, P.C.

(57) ABSTRACT

A mobile diagnosis device comprised of an ECG unit (1) to record an ECG signal (55), with the ECG unit (1) being connected or connectible to two or more ECG electrodes (27, 28) to dissipate electrical signals from a patient's body, and comprised of a pulsoximetry unit (2) for simultaneous recording of a volume pulse signal (56), with the pulsoximetry unit (2) comprising at least one light source (17, 18) and at least one light sensor (20) for optical measurement of blood perfusion in the vascular system of a patient's body tissue, and comprised of a program-controlled evaluation unit (4) to evaluate the ECG signal (55) and the volume pulse signal (56). To provide such a diagnosis device that is suitable for auto-diagnosis of cardiovascular diseases, the device proposes that the evaluation unit (4) be appropriately equipped to allow for automatic recognition of R peaks (57) in the ECG signal (55), automatic recognition of extreme levels (58) in the volume pulse signal (56), and for determination of the time difference (60) between an R peak (57) and a successive extreme level (58) in the volume pulse signal (56). Furthermore, the evaluation unit (4) can be appropriately equipped to allow for determination of the time difference (61) between the main and secondary peak values (58, 59) in the volume pulse signal (56).

11 Claims, 10 Drawing Sheets

MOBILE DIAGNOSIS DEVICE

CROSS REFERENCE TO RELATED APPLICATIONS

Applicants claim priority under 35 U.S.C. §119 of German Application No. 10 2005 013 429.7 filed Mar. 21, 2005. Applicants also claim priority under 35 U.S.C. §365 of PCT/EP2006/002410 filed Mar. 16, 2006. The international application under PCT article 21(2) was not published in English.

BACKGROUND OF THE INVENTION

The present invention relates to a mobile diagnosis device comprised of an ECG unit to record an ECG signal, with the ECG unit being connected or connectible to two or more ECG electrodes to dissipate electrical signals from a patient's body, and comprised of a pulsoximetry unit for simultaneous recording of a volume pulse signal, with the pulsoximetry unit comprising at least one light source and at least one light sensor for optical measurement of blood perfusion in the vascular system of a patient's body tissue, and comprised of a program-controlled evaluation unit to evaluate the ECG signal and the volume pulse signal.

Cardio-vascular diseases are the main cause of death in nearly all industrialized countries, as is well known. A special rank is taken by arteriosclerosis, i.e. the pathological stenosis of blood vessels. Approx. 50% of patients suffering from ateriosclerosis are also affected by coronary heart disease. On account of the clearly recognizable progression of cardio-vascular diseases and the restricted therapeutical possibilities in the late stages of these diseases, it is intended to strive for the earliest possible diagnosis. To this effect it is necessary to realize and evaluate complex correlations in a cardio-vascular system. Both the heart and the blood vessels must be evaluated equally in their functional status to permit early diagnosis. A healthy vascular system can offset minor heart insufficiencies for years, as is well known, while a vascular system already affected by arteriosclerosis advances circulatory decompensation.

The ECG (electrocardiogram) might be the most frequently applied examination modality for diagnosis of cardio-vascular diseases. By means of an ECG device, electrical signals are dissipated with two or more ECG electrodes from the body of a patient to be examined. The ECG thus obtained reflects the bioelectrical voltages that occur during excitation spread and regression at the heart. The ECG contains numerous parameters that can be diagnostically evaluated. At the moment when the heart muscle contracts during a heart beat, the ECG shows an evident peak which is also designated as R peak. Furthermore, the ECG contains the so-called P wave which precedes the R peak. The R peak, in turn, is followed by what is called a T wave. The minimum levels in the ECG immediately before and immediately after the R peak are designated by Q and S, respectively. Those parameters of interest for cardio-vascular diagnostics are the duration of the P wave as well as the amplitude of the P wave, the duration of the PQ interval, the duration of the QRS complex, the duration of the QT interval as well as the amplitude of the T wave. Both from the absolute values of the a.m. parameters and from the ratios of these parameters, it is possible to draw conclusions on the health status of the cardiovascular system.

Capturing and recording of peripheral cardio-vascular parameters is feasible by what is called plethysmography. In plethysmography, blood-flow conditioned volume fluctuations of a peripheral blood vessel are measured. Nowadays, the NIRP method (near infrared photo plethysmography) has won its way. The diagnostic modalities applied therein are briefly called pulsoximeters. Such pulsoximeters typically comprise two light sources which radiate red and/or infrared light of a different wavelength into the human body tissue of a patient. The light is scattered in a patient's body tissue and partly absorbed. The scattered light is detected by means of a light sensor in form of an appropriate photocell. Commercial pulsoximeters, on the one hand, typically use light in a wavelength range of 660 nm. Within this range, the light absorption of oxyhemoglobin and deoxyhemoglobin differs substantially. The intensity of the scattered light detected by means of the light sensor varies accordingly, dependent upon how strongly the examined body tissue is supplied with blood rich in oxygen or poor in oxygen, respectively. On the other hand, light in a wavelength range of 810 nm is commonly used. This light wavelength lies in what is called near infrared spectral range. The light absorption of oxyhemoglobin and deoxyhemoglobin within this spectral range is essentially equal. Prior art pulsoximeters are capable of generating a volume pulse signal that reflects the blood volume which is variable during a heart beat and which passed by the micro-vessel system captured by the pulsoximeter. When different light wavelengths are employed in the afore-mentioned spectral ranges, it is possible to draw conclusions from the different light absorption to evaluate the oxygen content of blood (oxygen saturation). Commonly applied pulsoximeters are either employed at the patient's finger tip or at the lobe of the ear. The volume pulse signal is then generated from the blood perfusion of the micro-vessel system in these regions of the body tissue.

A prior art disclosed in U.S. Pat. No. 4,960,126 is an ECG-synchronized pulsoximeter. The prior art equipment is comprised of an ECG unit and a pulsoximetry unit. With the prior art diagnosis device, the ECG unit is utilized to determine the heart beat cycle by detection of R peaks in the ECG signal. The duration of the heart beat cycle is then taken as the basis in determining the oxygen saturation by means of the pulsoximetry unit. Thereby, it is intended to improve signal averaging and reduce motion-induced artefacts. On the whole, a more reliable determination of the value of oxygen saturation of blood is achieved thereby as compared with conventional pulsoximeters.

Known combined ECG and pulsoximetry devices allow for determining a plurality of cardiovascular parameters. Based upon these data, a practicing doctor can make a comprehensive cardio-vascular diagnosis, to be true. But prior art devices have a drawback in that they do not allow for an automatic establishment of a preliminary diagnosis of imminent or already existing cardio-vascular diseases. For this reason, prior art devices cannot be readily employed by patients for auto-diagnosis either.

Against this background, it is the object of the present invention to provide a diagnosis device that allows for an (at least coarse) status and trend diagnosis of the cardio-vascular system. This device is intended to be capable of indicating to a patient an early auto-diagnosis of a cardio-vascular disease without posing excessive demands on a patient in terms of evaluating a plurality of diagnostic parameters.

SUMMARY OF THE INVENTION

The present invention solves this task based upon a mobile diagnosis device of the type and nature mentioned hereinabove in that the evaluation unit is configured
  for automatic detection of R peaks in the ECG signal,
  for automatic detection of extreme values in the volume pulse signal, and for determination of the time difference between an R peak in the ECG signal and an extreme value following next in the volume pulse signal.

The present invention is based upon the finding that a combination of the ECG signal with the volume pulse signal in the combined diagnosis device comprised of an ECG unit and a pulsoximetry unit allows for a simple automatic status diagnostics of the cardiovascular system. By means of an appropriate program control, the evaluation unit of the inventive mobile diagnosis device is capable of automatically recognizing the R peaks in the ECG signal. Thereby, the exact moment of a heart beat is automatically determined. Furthermore, based upon its inventive program control, the evaluation unit is capable of recognizing extreme levels, i.e. minimum or maximum levels, in the volume pulse signal. Based upon the extreme levels in a volume pulse signal, the moment of arrival of a pulse wave triggered with a heart beat can be ascertained at the peripheral measurement location covered by the pulsoximetry unit. After all, it is thus possible to determine the time-relevant interval between an R peak in the ECG signal and a successive extreme level in the volume pulse level. This time-relevant interval is a measure of what is called pulse wave velocity. On the basis of pulse wave velocity, it is possible to make a statement on blood pressure. For a shortening in pulse wave velocity is accompanied by an increase in blood pressure, while an extension in pulse wave velocity is indicative for a decrease in blood pressure. However, an exact assessment of blood pressure based on pulse wave velocity is impossible, it is merely possible to indicate tendencies. Furthermore, the pulse wave velocity is dependent on blood density and, in particular, on the elasticity of blood vessel walls. From the elasticity of blood vessels, in turn, conclusions can be drawn concerning a possibly existing arteriosclerosis. Pulse wave velocity also depends on the inner diameter of arteria. Thereby it is possible to characterize the supply of blood at the relevant location of medical examination (e.g. on a patient's arm), assuming constant elasticity and constant density of blood. By combining the ECG signal with the volume pulse signal in the automatic evaluation, the inventive diagnosis device is autonomously able to make a functional evaluation of a patient's vascular system. Based upon automatically evaluated signals, the inventive diagnosis devices can roughly assess a patient's cardiovascular status and generate an adequate warning signal to a patient, if there is any indicative sign of arteriosclerosis. Thus, a patient can employ the inventive diagnosis device for auto-diagnosis. There is no necessity for a differentiated evaluation of the various cardio-vascular parameters determined by the device that in most cases would pose excessive demands on a patient.

In accordance with a purposive embodiment of the inventive diagnosis device, the evaluation unit is furthermore appropriately equipped to allow for
  determination of blood oxygen saturation from the volume pulse signal,
  determination of ventricular heart frequency rate from the ECG signal,
  and/or for determination of plethysmographic heart frequency rate from the volume pulse signal.

A determination of blood oxygen saturation, ventricular, plethysmographic heart frequency rate allow for making a further and more refined status diagnostics of the cardio-vascular system. With the inventive diagnosis devices it is possible to automatically determine the absolute values of the heart frequency rate, heart frequency variability, and the corresponding arrhythmii of the heart. In this manner, arrhythmii such as Sinus Tachycardia, Sinus Bradycardia, Sinus Arrest and so-called Escape Beats can be ascertained. Based upon the ECG signal, it is moreover possible to make statements on the time-relevant duration of an auricular systole of the heart with one heart beat, the time-relevant duration of the ventricular contraction as well as the duration of the relaxation of the ventricle, etc. Besides, pre-diagnoses concerning so-called blocks in the line of the electrical excitation signals at the heart (AV-Block, Bundle Branch-Block etc.) and also concerning circulatory disorders or infarcts can be established. Other irregularities in the pulse course are detectible based on the volume pulse signal. Blood oxygen saturation, too, represents a significant parameter in status diagnostics of the cardio-vascular system. Based on blood oxygen saturation, conclusions can be drawn with regard to the efficiency and adaptability of the cardio-vascular system.

It is of advantage if the evaluation unit of the inventive diagnosis device is furthermore appropriately equipped to allow for an automatic recognition of main and secondary peak values in the volume pulse signal, for determination of the amplitudes of the main and secondary peak values, and for determination of the time-relevant interval between the main and secondary peak values. This enables an automatic examination of the dicrotism of the volume pulse signal. Dicrotism is defined as the double-peak configuration of the blood pressure course in distant blood vessels. Dicrotism is caused by an overlapping of the pulse wave proceeding from the heart with a regressive pulse wave from the reflexion of the pulse wave at vessel partitions or less elastic vessel sections. It is known that with a diminishing elasticity and thus with an enhancing degree of an arteriosclerosis the time-relevant interval between the main and secondary peak values in the plethysmographic signal becomes less, with the secondary maximum losing it intensity at the same time. By determining the time interval between main and secondary peak values and by determining the relative amplitudes of main and secondary peak values, other significant parameters are thereby available that can be utilized with the inventive diagnosis device to automatically detect indicative signs of arteriosclerosis.

The secondary maximum levels in the volume pulse signal are caused above all by a reflexion of the pulse waves at the lower extremities. Therefore, the time-relevant interval between main and secondary peak values is mainly determined by the properties of the aorta. Thereby it is possible to determine a second pulse wave velocity, i.e. the pulse wave velocity in the aorta, while the first pulse wave velocity is determined at the relevant measuring point (e.g. on a patient's arm), as has been outlined hereinabove. Hence, with the inventive diagnosis device, it is possible to advantageously determine two different pulse wave velocities and evaluate these to diagnose diseases (individually or in combination).

Expediently the inventive diagnosis device is furthermore comprised of sensors to measure a patient's body temperature, the ambient temperature, and/or humidity in air. These parameters are particularly important for calibrating the ECG unit and the pulsoximetry unit of the inventive diagnosis device.

A particularly purposive embodiment of the inventive diagnosis device is provided if it is comprised of a memory unit to memorize the parameters determined during a measurement by means of the evaluation unit while simultaneously storing the date and/or time of the measurement. By means of a memory unit, it is possible to follow-up and document the course of a disease of the cardio-vascular system on the one hand and the effects of a corresponding therapy. On the other hand, the data stored in the memory unit of the diagnosis device can be read-out and evaluated by the practicing doctor in order to allow for a detailed status diagnostics of the cardio-vascular system by the doctor. Expediently the inventive diagnosis device is comprised of a data transfer interface to transfer the data stored in the memory unit of the diagnosis device into the doctor's personal computer. This interface can be a usual wired or wireless interface (for example one operating to the Bluetooth standard).

Furthermore it is purposive if the inventive diagnosis device is comprised of a diagnosis unit that is appropriately equipped to allow for a determination of the status of a patient's cardiovascular system from the parameters determined by means of the evaluation unit. Accordingly, the diagnosis device has a modular setup. The evaluation device is merely in charge of evaluating captured signals in order to determine thereof those parameters required for diagnostics in the manner described hereinabove. These parameters are then processed by the diagnosis unit of the diagnosis device in order to draw conclusions therefrom with regard to the status of the cardiovascular system. The diagnosis unit is also in charge of automatically recognizing the existence of arteriosclerosis and generating a corresponding warning signal to the patient, if required.

It is of advantage if the diagnosis unit of the inventive diagnosis device is furthermore appropriately equipped to be able to determine trends with regard to a change in the status of a patient's cardio-vascular system from the time-relevant variation of the parameters stored by means of the memory unit. In some cases, it is impossible to draw direct conclusions on potential diseases from the parameters determined by means of the evaluation unit of the diagnosis device. However, a change in the parameters, for example a continuous increase in pulse wave velocity, may be indicative for a developing cardio-vascular disease at an early stage. Such trends can be utilized for automatic recognition of diseases, if the diagnosis device is repeatedly utilized by a patient over an extensive period of time, with the parameters automatically determined by the evaluation unit being stored by means of the memory unit of the diagnosis device.

The diagnosis unit of the inventive diagnosis device can expediently be equipped to compute an elasticity parameter from the time-relevant interval between an R peak in the ECG signal and a successive extreme level in the volume pulse signal, with the elasticity parameter representing a measure for the elasticity of a patient's blood vessels. The pulse wave velocity (PWG) is proportional to the square root from the quotient of the elasticity of blood vessels κ and the specific density of blood ρ. The applicable formula reads as follows:

$$PWG = \sqrt{\kappa h/d\rho}.$$

Wherein κ is the elasticity of blood vessels, h is the wall thickness of veins, d is the diameter of vessels, and ρ is the density of blood. From this correlation, the elasticity κ can be computed by means of the diagnosis unit, if the specific density of blood ρ and the other parameters are assumed to be constant. From the elasticity parameter alone or in combination with other parameters of the cardio-vascular system that can be determined by the inventive diagnosis device, it is possible to draw conclusions on arteriosclerosis.

In accordance with a purposive embodiment of the present invention, the diagnosis device is comprised of a display unit to display the ECG signal, the volume pulse signal, and the parameters determined by means of the evaluation unit. A patient utilizing the diagnosis device and/or the practicing doctor can read-out all values comfortably from the display unit. At the same time, it is possible to check the diagnosis device for proper functioning.

According to a preferred embodiment of the inventive diagnosis device, the ECG unit, the pulsoximetry unit, and the evaluation unit are accommodated in a common casing. Thus the diagnosis device is of a compact setup and can be utilized as a mobile device at any time.

It is particularly expedient if the ECG electrodes as well as the light source and the light sensor of the pulsoximetry unit are so arranged on the exterior side of the casing that a patient can touch with one hand a first ECG electrode and with the other hand a second ECG electrode and simultaneously the light sensor. A patient can hold tight the diagnosis device configured in this manner with both hands and watch the display of the diagnosis device at the same time. The ECG derivation then proceeds from the patient's left and right hand. The pulsoximetry unit concurrently captures the volume pulse signal at one of these two hands that touch the casing. This configuration has the advantage in that it is not necessary to connect additional electrodes through cable connections to the diagnosis device. All components form a compact unit. Faults in operating the device, more particularly on connecting the ECG electrodes and affixing a pulsoximeter to a patient's body are ruled out.

Likewise, the ECG signal can be taken-up through at least two external electrodes which can be glued directly on a patient's body. This arrangement has the advantage that it keeps a patient's hands free, for example to keep position or get support on an ergometer.

Alternatively it is possible to accommodate the light source and the light sensor in a measuring head separated from the casing, i.e. in such a manner that the light sensor can be put on a patient's body at arbitrary measuring points. This allows for examining microvascular perfusion not only on a patient's hand but at arbitrary measuring points on a patient's body.

The present invention furthermore relates to a method for acquisition and evaluation of a patient's cardio-vascular parameters, wherein an ECG signal is captured by means of an ECG unit which is connected with two or more ECG electrodes for dissipation of electrical signals from a patient's body, a volume pulse signal is simultaneously captured by means of a pulsoximetry unit which is comprised of at least one light source and at least one light sensor for optical measurement of blood perfusion in the vascular system of a patient's body tissue, and the ECG signal as well as the volume pulse signal are evaluated by means of a program-controlled evaluation unit.

The task and objective underlying the present invention is solved and achieved in such a method in that by means of the evaluation unit R peaks in the ECG signal are automatically recognized, extreme levels in the volume pulse signal are automatically recognized, and the time-relevant interval between an R peak in the ECG signal and a successive extreme level in the volume pulse signal is determined.

An actually known diagnosis device comprised of an ECG unit and a pulsoximetry unit can be employed by way of an adequate program control of the evaluation unit in accordance with the present invention. A computer software for the evaluation unit of such a diagnosis device includes instructions for automatic recognition of R peaks in the ECG signal, for automatic recognition of extreme levels in the volume pulse signal, and for determination of the time-relevant distance between an R peak in the ECG signal and a successive extreme level in the volume pulse signal.

Moreover, the computer software can comprise instructions for computation of the pulse wave velocity from the time-relevant interval between an R peak in the ECG signal and a successive extreme level in the volume pulse signal. The pulse wave velocity represents the central parameter which the status diagnostics of the cardio-vascular system with the inventive diagnosis device is mainly based upon.

It is advantageous for the computer software to also contain instructions for automatic recognition of main and secondary peak values in the volume pulse signal, to determine the time-relevant interval between main and secondary peak values, and to compute a second pulse wave velocity from the time-relevant interval between the main and secondary peak values. This second pulse wave velocity is the pulse wave velocity in the aorta.

A computer software of the type described hereinabove can also be utilized in the sense of the present invention to evaluate an ECG signal and a volume pulse signal by means of a usual PC.

BRIEF DESCRIPTION OF THE DRAWINGS

Examples for embodiments of the present inventions are explained in greater detail in the following, taking reference to the relevant drawings, wherein.

DETAILED DESCRIPTION

Figure 1:
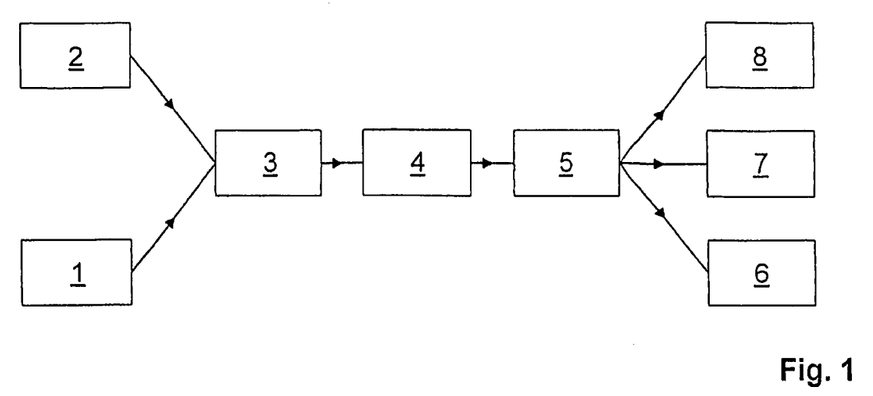
FIG. 1 shows the setup of the inventive diagnosis device based on a block diagram.

FIG. 1 elucidates the essential components of the inventive mobile diagnosis device and their co-action. The diagnosis device is comprised of an ECG unit 1 and a pulsoximetry unit 2. The ECG unit 1 is connectible by ECG electrodes not shown more detailedly in FIG. 1 for dissipation of electrical signals from a patient's body. The ECG signals captured by the ECG unit 1 are transmitted to an analysis unit 3. The pulsoximetry unit 2 serves for optical measurement of blood perfusion in the micro-vascular system of a patient's body tissue. The volume pulse signals captured by the pulsoximetry unit 2 at two different light wavelengths are also transmitted to the analysis unit 3. By means of the analysis unit 3, the signals from the pulsoximetry unit 2 and from the ECG unit 1 are pre-processed. In particular, the signals pass through a bandpass filter in order to filtrate interferences in a range of net frequency from 50 and/or 60 Hz. Furthermore, the signals from the pulsoximetry unit 2 are subjected to averaging in order to reduce the signal-to-noise ratio. Having passed the analysis unit 3, the pre-processed signals from the ECG unit 1 and from the pulsoximetry unit 2 come into an evaluation unit 4. By means of the evaluation unit 4 the parameters required for cardio-vascular diagnostics are extracted from the signals. To this effect, the evaluation unit 4 has an appropriate program control. By means of this program control, R peaks in the ECG signal are automatically recognized, extreme levels in the volume pulse signal are automatically recognized, and the time-relevant interval between an R peak in the ECG signal and the successive extreme level, e.g. the nearest minimum in terms of time, in the volume pulse signal is determined. Furthermore, the blood oxygen saturation is determined from the volume pulse signals of the pulsoximetry unit 2. Determined from the time-relevant intervals between R peaks in the ECG signal is the ventricular heart frequency rate. The plethysmographic heart frequency rate is determined from the volume pulse signal. Furthermore, the evaluation unit 4 is appropriately equipped by its program control to automatically recognize main and secondary peak values in volume pulse signals as well as to determine the amplitudes of main and secondary peak values. Besides, the time-relevant intervals between main and secondary peak values in volume pulse signals are determined by means of the evaluation unit 4, whereof the pulse wave velocity in the aorta can be ascertained, as has been outlined hereinabove. The parameters thus determined by the evaluation unit 4 are passed on to a diagnosis unit 5. The diagnosis unit 5 is appropriately equipped to allow for a determination of the status of the cardio-vascular system from those parameters determined by means of the evaluation unit 4. Through a suitable program control, the diagnosis unit 5 interprets the relevant parameters in order to assess the quality of a patient's vascular system and to ascertain whether the parameters determined are indicative signs for an existing arteriosclerosis. The diagnosis unit 5 evaluates the heart frequency rate in order to ascertain whether there is a bradycardia or a tachycardia. Other irregularities of the heart beat such as for example extrasystoles, can also be ascertained by means of the diagnosis unit 5. Furthermore, the diagnosis unit 5 compares the ventricular heart frequency rate with the plethysmographic heart frequency rate in order to detect pulse deficits, if any. But in particular, the diagnosis unit 5 is appropriately equipped with its program control to compute an elasticity parameter from the time-relevant interval between an R peak in the ECG signal and a successive extreme level in the volume pulse signal. Accordingly, the elasticity parameter is a measure for the elasticity of a patient's blood vessels. By involvement of the other parameters determined by means of the evaluation unit 4, more particularly those parameters concerning the dicrotism of the volume pulse signal, the diagnosis unit 5 can analyse the cardiovascular status of a patient autonomously and with high reliability. Thereby, the inventive diagnosis device is helpful to allow for an early diagnosis of a coronary heart disease. The parameters determined by means of evaluation unit 4 as well as the data derived therefrom by means of the diagnosis unit 5 are ultimately stored in a memory unit 6 of the inventive diagnosis device, i.e. by simultaneously storing the date and time of each measurement. All the data and parameters thus obtained can be displayed by means of a display unit 7. In particular, display unit 7 displays the ECG signal, the volume pulse signal, and the pulse wave velocity. Besides, an interface 8 is provided for to establish a connection between the diagnosis devices and a computer. Via interface 8 all the data and parameters, particularly those data and parameters stored in the memory unit 6 can be transmitted to a PC (not shown in detail) of the practicing doctor. There, the data can be analysed more detailedly. In particular, those data and parameters recorded with the diagnosis device over an extensive period of time can be investigated for changes in order to be able to derive therefrom certain trends with regard to the development of a patient's existing disease. Moreover, it is possible to follow-up the success of a therapy. Furthermore, it is possible to utilize the inventive diagnosis device also as a mere measuring data acquisition and transmission unit and to transfer recorded signals, for example directly to a doctor's PC by means of which the corresponding evaluations, computations, and representations (see further below) can then be carried out (possibly more quickly and more comfortably.)

Figure 2:
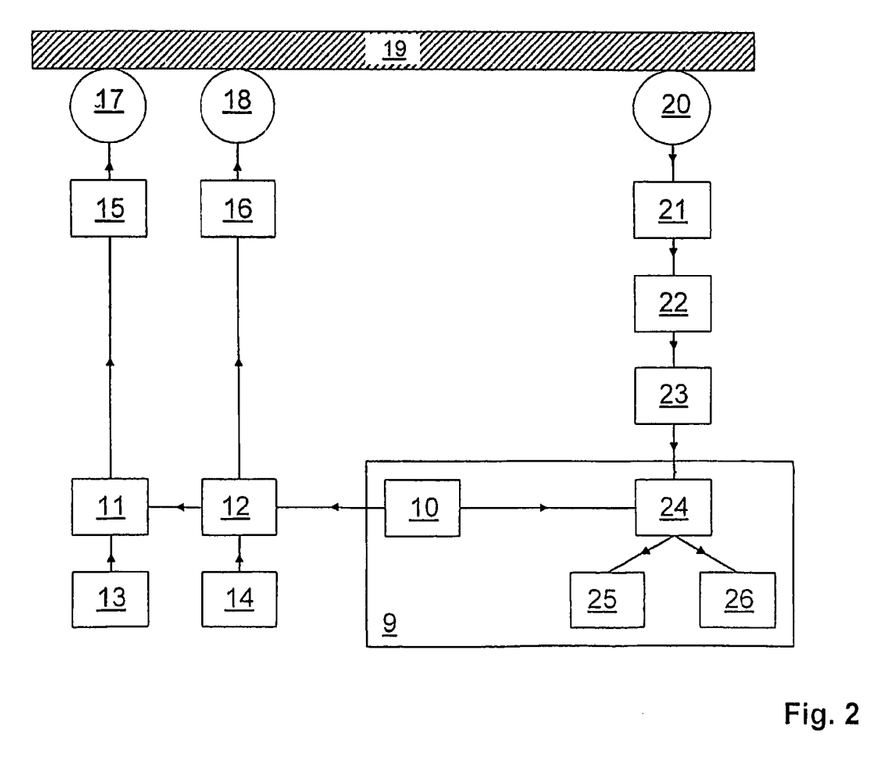
FIG. 2 shows a block diagram representation of the pulsoximetry unit of the inventive diagnosis device.

FIG. 2 illustrates the setup of the pulsoximetry unit 2 of the inventive diagnosis device. The pulsoximetry unit 2 is comprised of a micro-controller 9. An integral part of the micro-controller 9 is a timing generator 10, which activates an infrared modulator 11 and a red modulator 12. By means of the modulators 11 and 12, the supply voltages of adjustable voltage supplies 13 and 14 are modulated. Modulated voltages are conducted through current/voltage converters 15, 16 to a light-emitting diode 17 emitting an infrared light and to a light-emitting diode 18 emitting a red light. The timing generator 10 ensures that the light-emitting diodes 17 and 18 are alternately turned on and off. Thus, a patient's body tissue is alternately radiated with red and infrared light. In the body tissue 19, the light is scattered and absorbed corresponding to the oxyhemoglobin and/or deoxyhemoglobin content of blood that flows through the tissue 19. The scattered light is registered by a photodetector (a photodiode) 20. The photon flux of the photodetector 20 is converted by means of a converter 21 into a voltage, amplified by means of an amplifier 22, and transformed by means of an analog/digital transducer 23 into a digital signal. The digital signal is then passed on to an infrared/red demodulator 24 which is a component of the micro-controller 9. The infrared/red demodulator 24 is linked to the timing generator 10. The demodulator 24 divides the digital signal into two volume pulse signals 25 and 26. The signal 25 represents the absorption of infrared light in the tissue 19, while the signal 26 is allocated to the absorption of the red light in the tissue 19.

Figure 3:
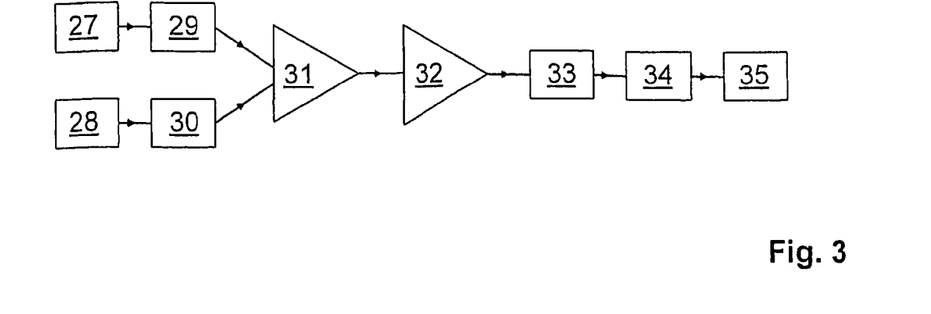
FIG. 3 shows a block diagram representation of the ECG unit.

Based upon FIG. 3 the setup of the ECG unit 1 of the inventive diagnosis device is explained. Connected to the ECG unit 1 are two ECG electrodes 27 and 28. The signals captured by means of electrodes 27 and 28 initially pass through high-pass filter 29 and 30. The boundary frequency of the high-pass filters 29 and 30 preferably ranges between 0.05 and 0.5 Hz. The filtered signals are then fed to a differential amplifier 31. It is extinguished by a high common-mode rejection which is purposive to reduce motion artefacts in the ECG signal. The differential amplifier 31 is succeeded by another amplifier 32 with a variable amplifying factor. The analog signal thus amplified is transformed by means of an analog/digital transducer 33 into a digital signal that is fed to a micro-controller 34 (which may be identical to the micro-controller 9). Finally, a filtration 35 of the digital signal is carried out in order to filtrate interferences of the signal at a net frequency of 50 and/or 60 Hz from the ECG signal.

Figure 4:
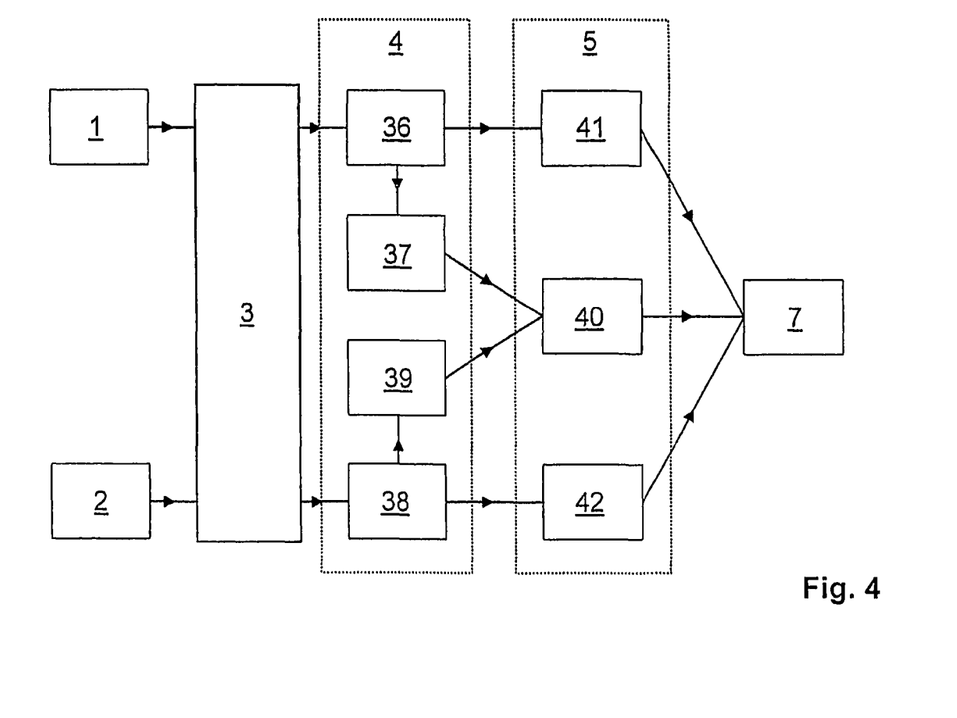
FIG. 4 illustrates the determination of the pulse wave velocity based on a process diagram.

The principle functional mode of the inventive diagnosis device is elucidated in FIG. 4. The signals captured by ECG unit 1 and pulsoximetry unit 2 and processed by means of analysis unit 3 are evaluated by means of evaluation unit 4, as has been outlined hereinabove. To this effect, the evaluation unit incorporates an appropriate program control which in a process step 36 initially analyses the ECG signal and determines various time intervals of the PQRST complex. In particular, the R peaks in an ECG signal are recognized in a process step 36. By access to a real-time clock of the inventive diagnosis device which is not shown in greater detail in these figures, the exact points of time of the detected R peaks are determined in a process step 37. Furthermore, the program control of the evaluation unit 4 is comprised of a dicrotism calculation routine 38. It is in charge of automatically recognizing main and secondary peak values in the digital volume pulse signals, and of determining the amplitudes of the main and secondary peak values as well as the time intervals between the main and secondary peak values. Another routine 39, in turn, by access to the real-time clock of the diagnosis devices, determines the exact point of time for each detected primary maximum level. The program control of the diagnosis unit 5 is comprised of a routine 40 for computation of an elasticity parameter from the time-relevant interval between the R peaks determined by means of routine 37 and the points of time of primary maximum levels (and/or minimum levels) evidenced by the volume pulse signals and determined by means of routine 39. For example, as elasticity parameters, routine 40 determines the pulse wave velocity which is invertedly proportional to the time interval between an R peak in the ECG signal and the succeeding minimum in one of the volume pulse signals. The elasticity parameter represents a measure for the elasticity of a patient's blood vessels and is displayed by means of display unit 17. Furthermore, the diagnosis unit 5 is comprised of a routine 41 for evaluation of the ventricular heart beat from the digital ECG signal as well as a routine 42 to assess the oxygen saturation of blood from the digital plethysmographic signals. The ventricular heart frequency rate as well as the oxygen saturation are also displayed by means of the display unit 7.

The most important function of the inventive diagnosis device is the automatic early recognition of an arteriosclerosis disease, as has been outlined hereinabove. With the evaluation routine 38 of the evaluation unit 4 and with the diagnosis routine 40 of the diagnosis unit 5, three significant parameters are determined which are characteristic for the elasticity of a patient's blood vessels. Therefore, based on these three parameters, one can ascertain an existing arteriosclerosis and even the severity of an existing disease. These three parameters are the time difference between the main and secondary peak values in the volume pulse signal, the relative intensity of the main and secondary peak values in the pulse wave velocity resulting from the time difference between an R peak in the ECG signal and the successive extreme level in the volume pulse signal. Upon evaluation of these three parameters, the inventive diagnosis device generates a warning signal, if required, advising a patient, for example, to consult a doctor. The practicing doctor can then evaluate in detail those data stored in the memory unit 6 of the device and establish an appropriate therapy for the patient.

Figure 5:
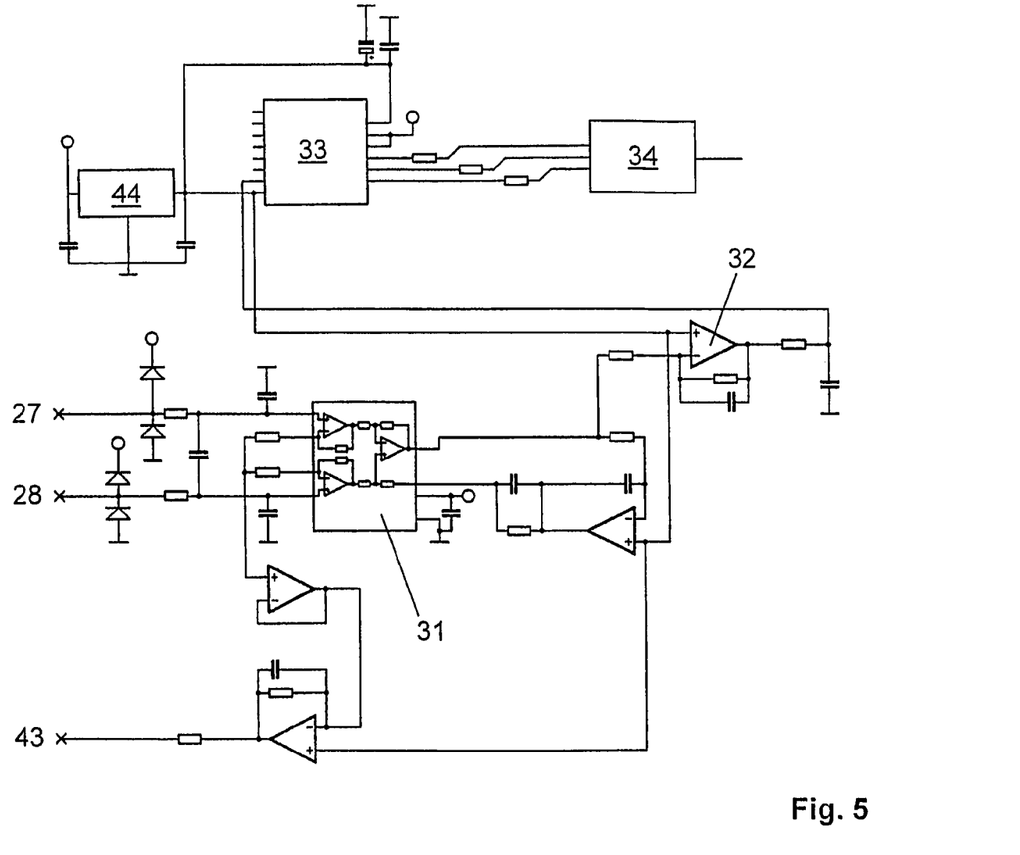
FIGS. 5 and 5a show a circuit diagram of the ECG unit of the inventive diagnosis device.
Figure 5A:
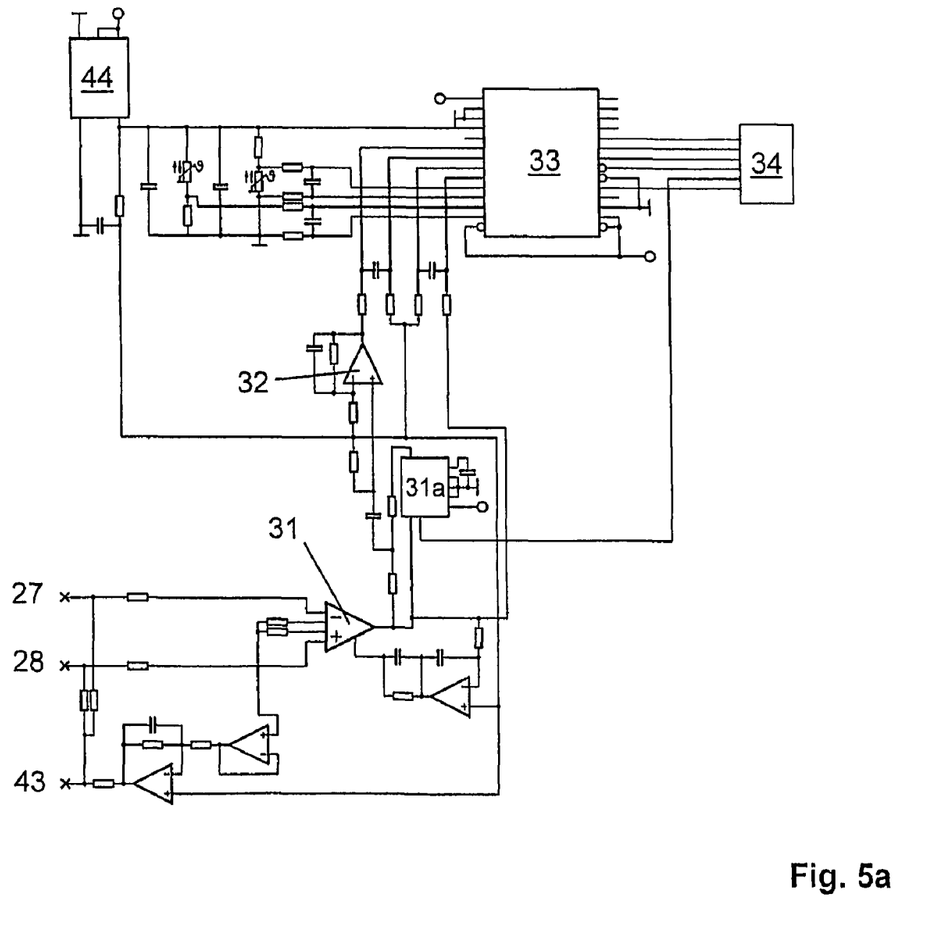

The diagram according to FIG. 5 shows the principle circuit engineering setup of the ECG unit 1 of the inventive diagnosis device. Via the two ECG electrodes 27 and 28, electrical signals are dissipated from a patient's body. Initially, these electrical signals are filtered by means of a passive network composed of diodes, capacitors, and resistors. Subsequently the signals are passed to the differential amplifier 31. It is distinguished by a high common-mode rejection. Thereby, interferences synchronously occurring at both electrodes are eliminated from the ECG signal. Via a third electrode 43, an inverted common-mode signal can be fed back to a patient, thus further reducing such signal interferences. The analog signal amplified by means of a variable amplifier 32 is then converted by means of the analog/digital transducer 33 into a digital ECG signal which is passed to the micro-controller 34. The analog/digital transducer 33 is linked to a reference voltage source 44. In accordance with FIG. 5a, a notch filter 31a is additionally provided for in order to filtrate the net frequency (50 Hz and/or 60 Hz) from the ECG signal.

Figure 6:
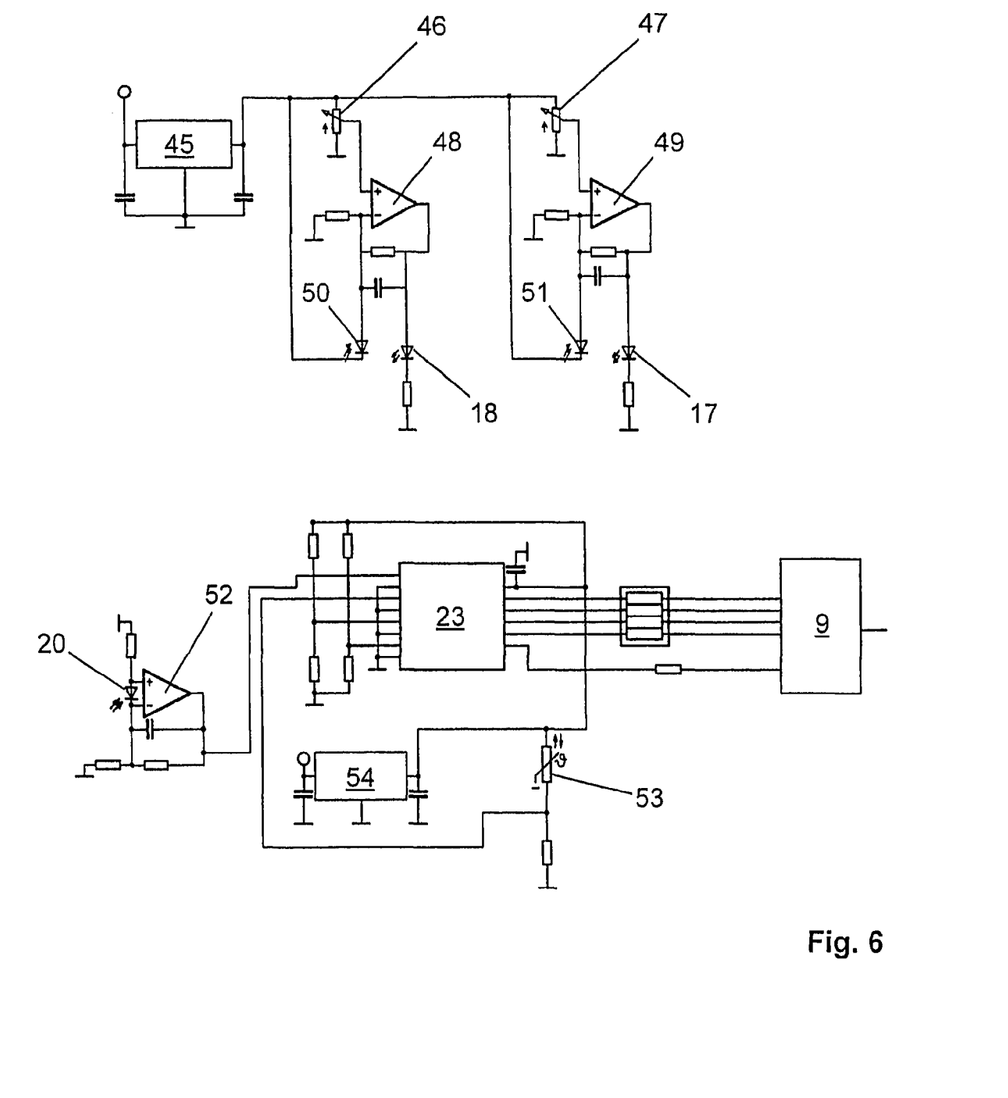
FIGS. 6 and 6a show a circuit diagram of the pulsoximetry unit of the inventive diagnosis device.
Figure 6A:
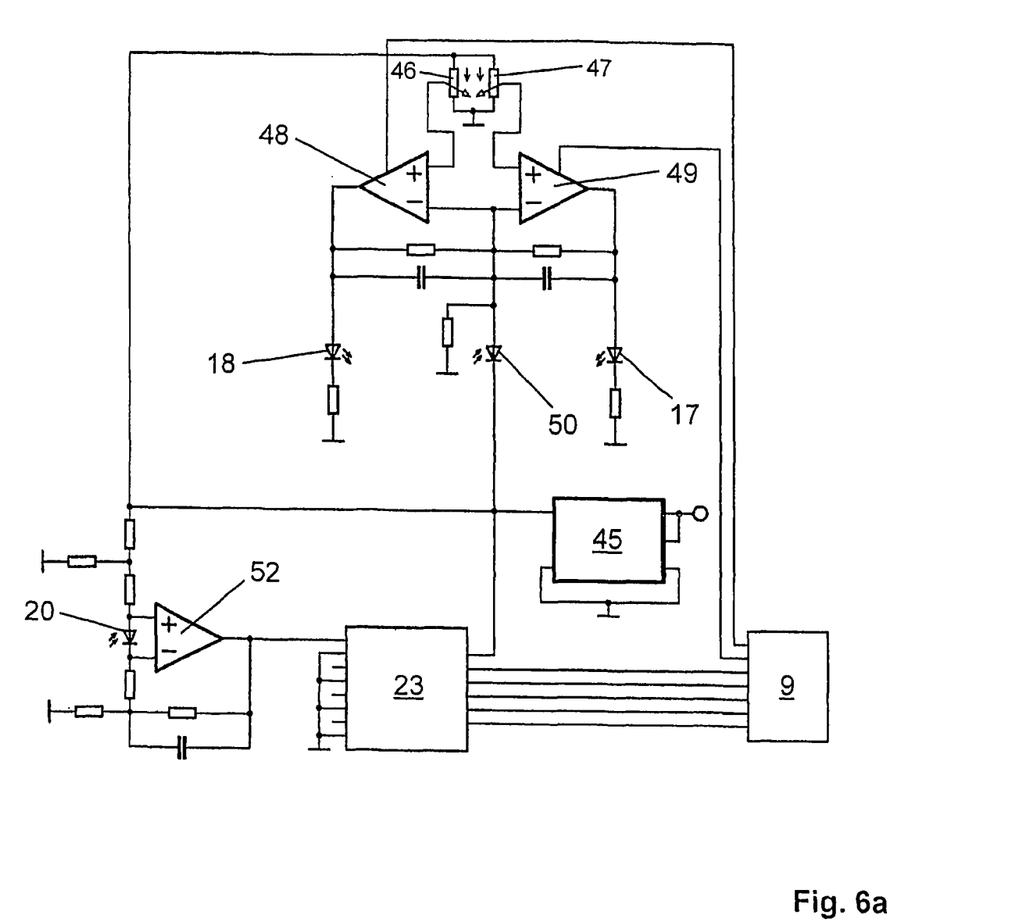

FIGS. 6 and 6a illustrate the principle circuit engineering setup of the pulsoximetry unit 2 of the inventive diagnosis device. The interconnection of the infrared LED 17 is identical to the interconnection of the red LED 18. Both parts are supplied with electric current through the reference voltage source 45. The activation of diodes 17 and 18 is effected through digital potentiometers 46 and 47. These are triggered by the micro-controller 9 of the pulsoximetry unit 2. The voltages at the outputs of operation amplifiers 48 and 49 together with the succeeding resistors determine those electric currents that stream through the light-emitting diodes 17 and/or 18. Photodiodes 50 and 51 are provided for which are connected to the operation amplifiers 48 and 49. The circuit variant according to FIG. 6a just needs one photodiode 50. Hereby a temperature-independent constant intensity of the light emitted from the diodes 17 and 18 is controlled. The light from light-emitting diodes 17 and 18 is detected by means of the photodiode 20. The photodiode 20 is connected to an operations amplifier 52 which converts the electric current through photodiode 20 into a voltage and amplifies it. This voltage is digitalized by means of the analog/digital transducer 23 and passed on to the pulsoximetry unit after it has been averaged. Furthermore, an NTC resistor 53 is provided for measurement of a patient's body temperature at the measuring point of the pulsoximetry unit. The NTC resistor 53 is linked to the analog/digital transducer 23. The NTC resistor 53 is a component part of a simple voltage divider which is charged with voltage through a reference voltage source 54. The reference voltage source 54 is simultaneously utilized for the analog/digital transducer 23. According to FIG. 6a, only one reference voltage source 45 is provided for. The circuit as per FIG. 5a corresponds to the variant shown in FIG. 6a in which an NTC resistor connected to the analog/digital transducer 33 is provided for which is missing in FIG. 6a.

Figure 7:
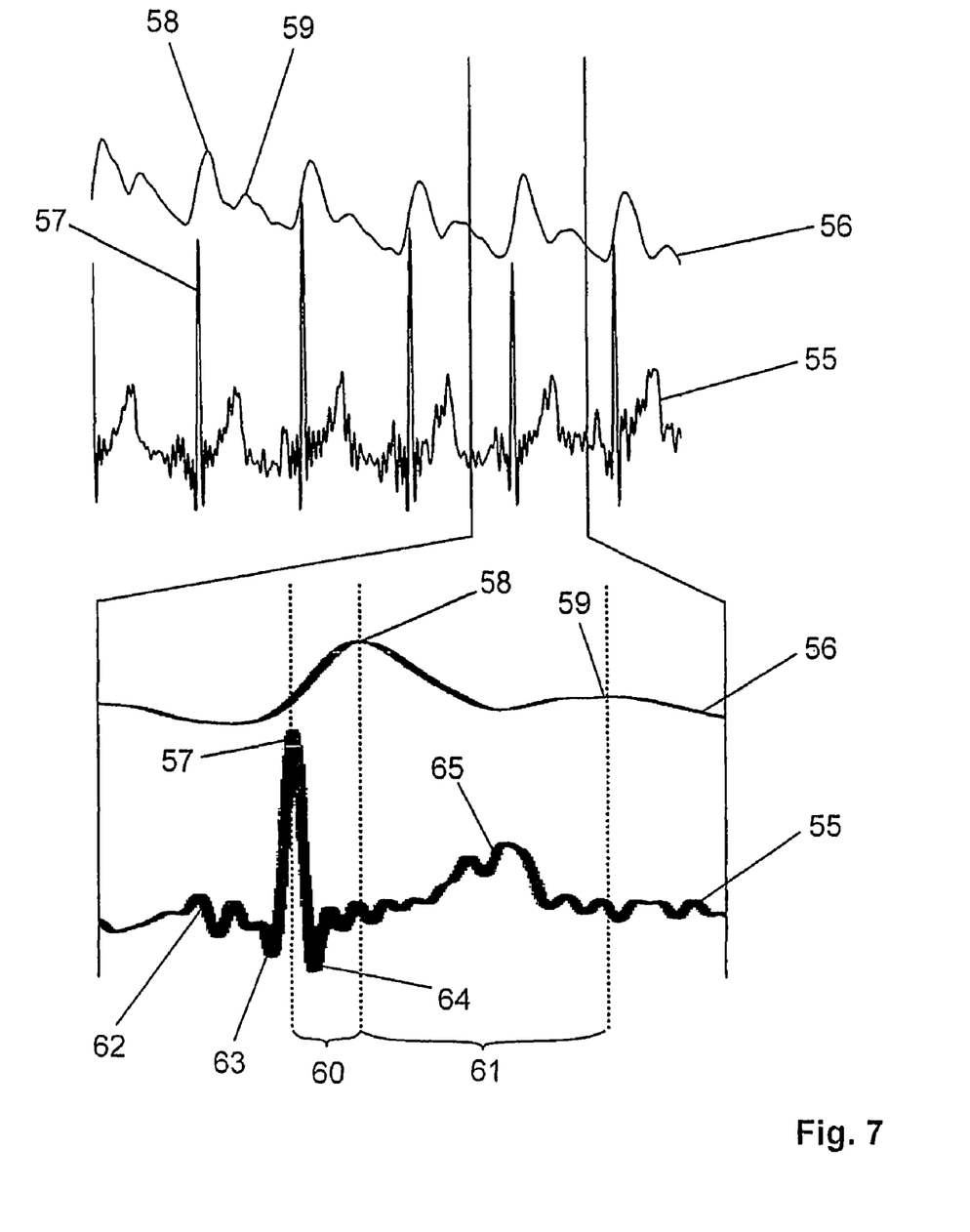
FIG. 7 represents a volume pulse signal together with an ECG signal.

FIG. 7 at top shows and ECG signal 55 together with a volume pulse signal 56 as a function of time. Signals 55 and 56 are simultaneously recorded with the inventive mobile diagnosis device. A plurality of R peaks 57 can be seen in the ECG signal 55. Each of the R peaks 57 indicates a ventricular heart beat. The primary maximum levels 58 and the secondary maximum levels 59 can be seen in the volume pulse signal. It evidences the dicrotism, i.e. the double peak configuration of the blood pressure course in the vessels covered by the pulsoximetry unit 2. The lower diagram of FIG. 7 shows a time clip from the ECG signal 55 and from the volume pulse signal 56 in a magnified representation. In this representation one can realize that there is a time difference 60 between the R peak 57 and the primary maximum level 58 of the volume pulse signal 56. This time difference is determined in accordance with the present invention. The time difference 60 depends on the pulse wave velocity. A large time difference suggests a low pulse wave velocity. A short time difference implies a high pulse wave velocity. A substantially increased pulse wave velocity, in turn, is indicative for the existence of arteriosclerosis, because the pulse wave velocity depends on the elasticity of blood vessels. To determine the pulse wave velocity, one can also take recourse to the time difference between the R peak 57 and a successive minimum of the volume pulse signal 56. This approach may have some advantages in terms of signal processing. Besides, the inventive diagnosis device evaluates the time difference 61 between the primary maximum level 58 and the secondary maximum level 59 of the volume pulse signal as well as the relative intensities of the primary maximum level 58 and secondary maximum level 59. From these parameters, one can draw a highly reliable conclusion as to the cardio-vascular status, more particularly with regard to the elasticity of blood vessels. Moreover, the P wave 62, the minimum levels and S 63 and/or 64 as well as the T wave 65 can be seen in the ECG signal 55. The time differences between these characteristic features of the ECG signal 55 are automatically evaluated by means of the inventive diagnosis device.

Figure 8:
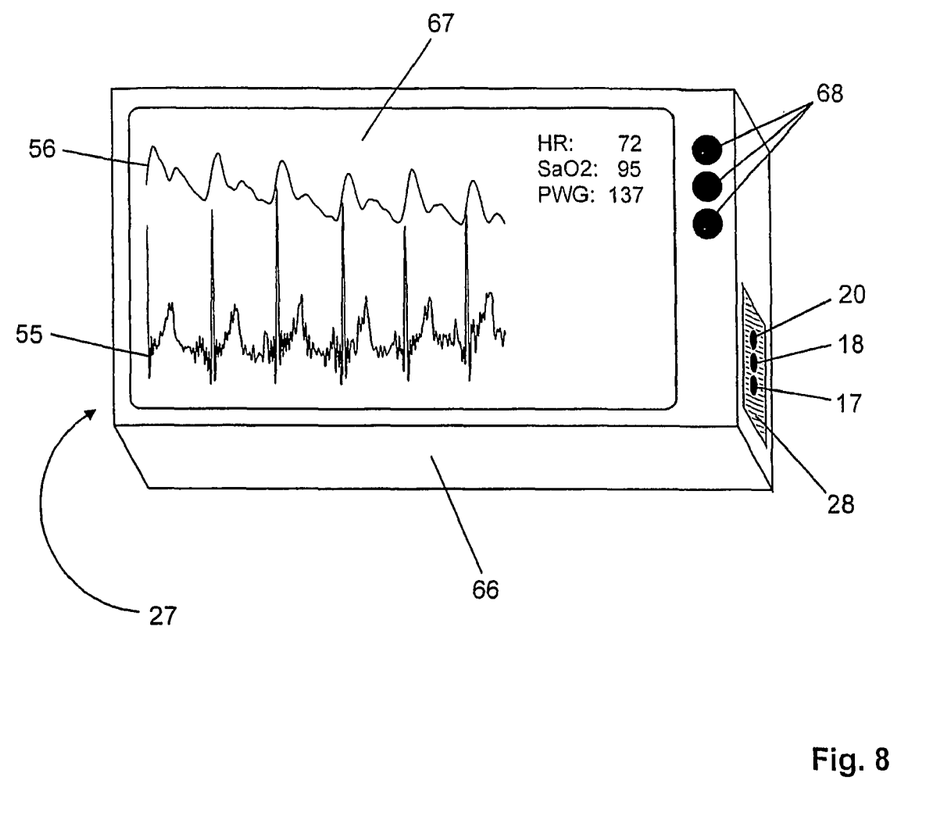
FIG. 8 shows a view of the inventive diagnosis device.

FIG. 8 shows a view of the inventive diagnosis device. It is comprised of a mainly quader-shaped casing 66, on the top side of which an LCD display 67 is arranged. It represents the display unit 7 of the diagnosis device. On the LCD display 67, the ECG signal 55 as well as the volume pulse signal 56 are graphically shown as a function of time. Concurrently, the ventricular heart frequency rate HR, the oxygen saturation of blood $SaO_2$ as well as the pulse wave velocity PWG are displayed. At the external side of casing 66, the two ECG electrodes 27 and 28 are arranged in such a manner that a patient can touch the electrode 27 with one hand and the electrode 28 with the other hand. Integrated in the electrode 28 are the light-emitting diodes 17 and 18 as well as the light sensor, i.e. the photodiode 20. Thus the pulsoximetry unit of the diagnosis device captures the volume pulse signal on the hand with which a patient touches the electrode 28. Arranged at the front side of casing 66 are the switches 68 to operate the diagnosis device.

Figure 9:
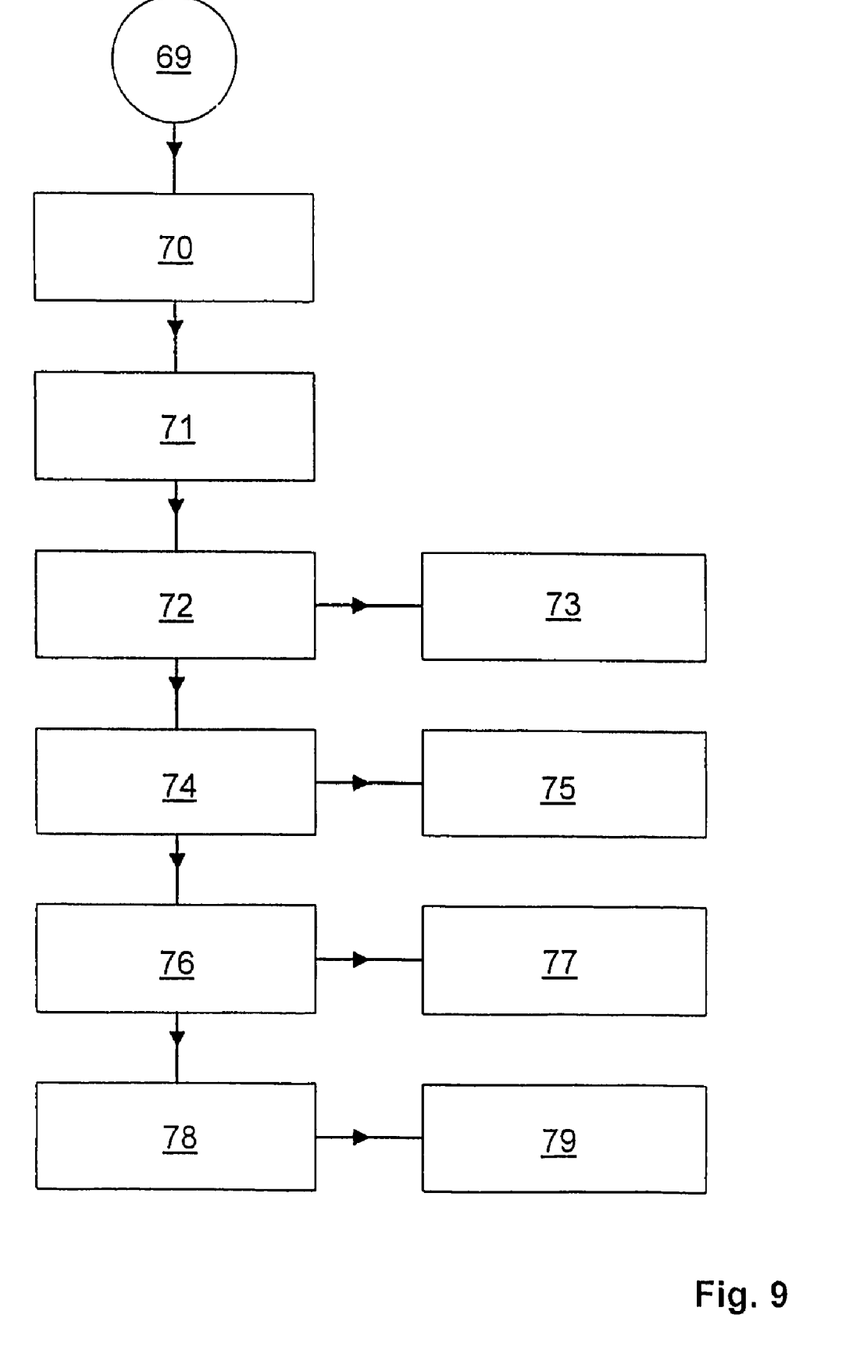
FIG. 9 shows a process diagram for evaluation of the ECG signal.

Based on FIG. 9 the algorithm implemented by the program control of the diagnosis device to evaluate the ECG signal 55 is explained in the following. As input data 69, the algorithm receives the digital ECG signal. Initially this signal is subjected to a low-pass filtration 70 in order to reduce the signal-to-noise ratio. In a next process step 71, the first time-related derivation of the ECG signal is formed. In process step 72, the R peaks are then automatically recognized based upon zero crossings of the derived signal from positive to negative values. From the time differences between the R peaks, the ventricular heart frequency rate is determined in process step 63. Two values of the heart frequency rate determined in immediate succession are compared with each other and checked for similarity. If the values range within certain boundaries, the ventricular heart frequency rate is displayed by means of display unit 7 of the diagnosis device. For example, after ten values of the heart frequency rate have been determined successively, a quality parameter is computed. This quality parameter Q is computed by applying the following formula: $Q=(N_s-1)/N_t$ Therein, $N_s$ is the number of heart frequency rate values considered to be similar to each other, and $N_t$ is the total number of determined heart frequency rate values. For example, $N_t$ is equal to ten. The quality parameter Q can also be displayed by display unit 7 of the diagnosis device. A small value of Q suggests an arrhythmical heart beat. In process step 74, the minimum levels in the ECG signal are determined immediately before and after the R peaks. Thereof, all parameters of the QRS complex of the ECG signal can be computed in process step 75. The first maximum level after each R peak is determined in process step 76. This maximum represents the T wave of the ECG signal. In process step 77, the QT interval, i.e. the time difference between the QRS complex and the T wave is computed. Finally, in process step 78, a maximum level between the T wave detected in process step 76 and the next R peak is determined. Hereof, in turn, the PR interval, i.e. the time difference between the P wave and the R peak can be computed in process step 79.

Figure 10:
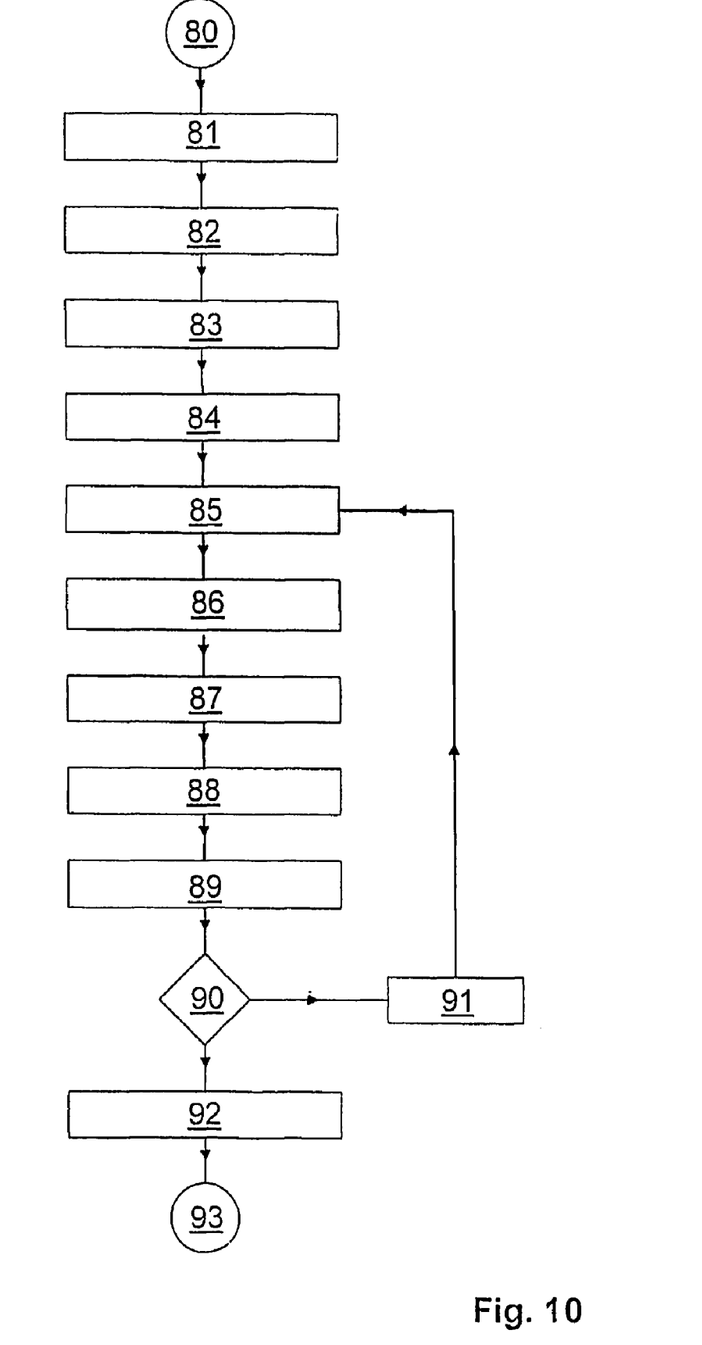
FIG. 10 shows a process diagram for evaluation of the volume pulse signal.

FIG. 10 elucidates the algorithm of the inventive diagnosis device for determination of the plethysmographic heart frequency rate. The algorithm proceeds from the digital volume pulse signal 80. It is initially filtered in a low-pass filter in a process step 81 in order to reduce the signal-to-noise ratio; subsequently the computation of the first time difference of the volume pulse signal is effected in process step 82. The first time-related derivation is again filtered in a low-pass filter in process step 83 to reduce the signal-to-noise ratio. A threshold value is stipulated in process step 84. For example, it may correspond to the absolute minimum of the volume pulse signal during a pre-settable time interval of e.g. 10 s. Then, in process step 85, the passages of the volume pulse signal through the threshold stipulated before are determined. In process step 86, local minimum levels in the derived signal between the passages through the threshold value defined before are determined. The time-related time interval between the local minimum levels in the derived signal corresponds to the time difference between the successive points of inversion in the original volume pulse signal. Therefore, the plethysmographic heart frequency rate can be computed in process step 87 from the time difference between the local minimum levels. Similarly to the determination of the ventricular heart frequency rate, the values of the plethysmographic heart frequency rate determined in chronological succession are checked for similarity in process step 88. A quality parameter is computed in process step 89 for a defined number of heart frequency rates determined in consecutive succession. This, too, is done similarly to the determination of the ventricular heart frequency rate. The quality parameter is evaluated in process step 90 and, if required, the threshold value is increased in process step 91 and the process is passed through again, commencing with process step 85. The repetition terminates as the quality parameter has reached a maximum valve. Then, in process step 92, an averaged plethysmographic heart frequency rate is computed from the individual heart frequency rate values. This value is then displayed together with the maximum quality parameter. This marks the end of the algorithm in process step 93.

The invention claimed is:

1. A mobile diagnosis device comprising:
    an ECG unit to record an ECG signal, with the ECG unit being connected to two or more ECG electrodes to measure electrical signals from a patient's body;
    a pulsoximetry unit for simultaneous recording of a volume pulse signal, the pulsoximetry unit comprising at least one light source and at least one light sensor for optical measurement of blood perfusion in the vascular system of a patient's body tissue;
    a program-controlled evaluation unit to evaluate the ECG signal and the volume pulse signal; and
    a casing that accommodates the ECG unit, the pulsoximetry unit and the evaluation unit, wherein the ECG electrodes and the light source and the light sensor of the pulsoximetry unit are arranged on an exterior surface of the casing, the ECG electrodes being connected to the device without a cable connection, wherein the light source and the light sensor of the pulsoximetry unit are integrated in a first ECG electrode of the ECG electrodes in such a manner that a patient can touch the first ECG electrode with one hand and a second ECG electrode with the other hand, while touching the light source and the light sensor at the same time;
    wherein said evaluation unit is appropriately equipped to allow for
    automatic recognition of R peaks in the ECG signal,
    automatic recognition of extreme levels in the volume pulse signal,
    and for determination of the time difference between an R peak in the ECG signal and a successive extreme value in the volume pulse signal.

2. A diagnosis device as defined in claim 1, wherein the evaluation unit is furthermore appropriately equipped to allow for
    determination of blood oxygen saturation from the volume pulse signal,
    determination of the ventricular heart frequency rate from the ECG signal,
    and/or for determination of the plethysmographic heart frequency from the volume pulse signal.

3. A diagnosis device as defined in claim 1, wherein the evaluation unit is appropriately equipped to allow for automatic recognition of main and secondary peak values in the volume pulse signal, for determination of the amplitudes of the main and secondary peak values, and for determination of the time difference between the main and secondary peak values.

4. A diagnosis device as defined in claim 1, comprising sensors to measure a patient's body temperature, the ambient temperature, and or the humidity in air.

5. A diagnosis device as defined in claim 1, comprising a memory unit to store the parameters determined by means of the evaluation unit during a measurement while simultaneously storing the date and/or time of the measurement.

6. A diagnosis device as defined in claim 1, comprising a diagnosis unit which is appropriately equipped to allow for determination of the status of the cardio-vascular system from the parameters determined by means of the evaluation unit.

7. A diagnosis device as defined in claim 6, wherein the diagnosis unit is furthermore appropriately equipped to determine trends concerning the status of a patient's cardio-vascular system from a change in the parameters stored by means of the memory unit.

8. A diagnosis device as defined in claim 6, wherein the diagnosis unit is appropriately equipped to compute an elasticity parameter from the time difference between an R peak in the ECG signal and a successive extreme level in the volume pulse signal, with the elasticity parameter representing a measure for the elasticity of a patient's blood vessels.

9. A diagnosis device as defined in claim 1, comprising an interface to link the diagnosis device to a computer.

10. A diagnosis device as defined in claim 1, comprising a display unit to display the ECG signal, the volume pulse signal, and the parameters determined by means of the evaluation unit.

11. A method for recording and evaluating a patient's cardio-vascular parameters, wherein
    an ECG signal is captured by means of an ECG unit which is connected with two or more ECG electrodes for measurement of electrical signals from a patient's body,
    a volume pulse signal is simultaneously captured by a pulsoximetry unit which is comprised of at least one light source and at least one light sensor for optical measurement of blood perfusion in the vascular system of a patient's body tissue,
    wherein the ECG signal and the volume pulse signal are evaluated by means of a program controlled evaluation unit,
    wherein a casing is provided for accommodating the ECG unit, the pulsoximetry unit and the evaluation unit,
    wherein the ECG electrodes and the light source and the light sensor of the pulsoximetry unit are arranged on an exterior surface of the casing, the ECG electrodes being connected to the device without a cable connection, wherein the light source and the light sensor of the pulsoximetry unit are integrated in a first ECG electrode of the ECG electrodes in such a manner that a patient can touch the first ECG electrode with one hand and a second ECG electrode with the other hand, while touching the light source and the light sensor at the same time, and,
    wherein by means of said evaluation unit
    R peaks in the ECG signal are automatically recognized,
    extreme levels in the volume pulse signal are automatically recognized,
    and that the time difference between an R peak in the ECG signal and the successive extreme level in the volume pulse signal is determined.

* * * * *